(12) United States Patent
Eller et al.

(10) Patent No.: US 8,571,297 B2
(45) Date of Patent: *Oct. 29, 2013

(54) PRESCRIPTION BOTTLE IMAGING SYSTEM AND METHOD

(71) Applicant: Express Scripts, Inc., St. Louis, MO (US)

(72) Inventors: Charles E. Eller, Lake St. Louis, MO (US); Herbert A. Youngs, St. Peters, MO (US)

(73) Assignee: Express Scripts, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,148

(22) Filed: Oct. 16, 2012

(65) Prior Publication Data

US 2013/0039564 A1 Feb. 14, 2013

Related U.S. Application Data

(63) Continuation of application No. 13/158,608, filed on Jun. 13, 2011, now Pat. No. 8,295,582, which is a continuation of application No. 11/357,580, filed on Feb. 17, 2006, now Pat. No. 7,995,831, which is a continuation of application No. 10/354,269, filed on Jan. 30, 2003, now abandoned.

(51) Int. Cl.
*G06K 9/00* (2006.01)
*G09F 17/00* (2006.01)
*G06K 15/00* (2006.01)
*G01J 3/28* (2006.01)

(52) U.S. Cl.
USPC ............ 382/142; 235/375; 235/383; 356/326

(58) Field of Classification Search
USPC .................... 382/142; 235/375, 383; 356/326
See application file for complete search history.

(56) References Cited

U.S. PATENT DOCUMENTS

| | | | |
|---|---|---|---|
| 6,202,923 B1 * | 3/2001 | Boyer et al. | 235/375 |
| 2003/0174326 A1 * | 9/2003 | Rzasa et al. | 356/326 |

* cited by examiner

*Primary Examiner* — Amara Abdi
(74) *Attorney, Agent, or Firm* — Bryan Cave LLP

(57) ABSTRACT

The invention is directed to a prescription imaging system for capturing, storing and displaying images of prescription bottles during the prescription fulfillment process to monitor the quality of the fulfillment process. The system includes one or more pill cameras for capturing images of pills dispensed into one or more prescription bottles and one or more label cameras for capturing images of the bottle labels. The images are stored on a storage device in a database record. The images can be used to verify that the pills in each bottle correspond with the associated prescription.

17 Claims, 4 Drawing Sheets

PRESCRIPTION BOTTLE IMAGING SYSTEM AND METHOD

RELATED APPLICATIONS

This application is a continuation of and claims priority to U.S. patent application Ser. No. 13/158,608 filed Jun. 13, 2011 now U.S. Pat. No. 8,295,582 issued Oct. 23, 2012; U.S. patent application Ser. No. 10/354,269 filed Jan. 30, 2003 now abandoned; and U.S. patent application Ser. No. 11/357,580 filed Feb. 17, 2006 now U.S. Pat. No. 7,995,831 issued Aug. 9, 2011, the contents of which are incorporated herein by reference.

FIELD OF THE INVENTION

This invention generally relates to systems and methods for dispensing prescriptions. More specifically, this invention is directed to a prescription imaging system and method for capturing, storing and displaying images of prescription bottles before delivery to customers.

BACKGROUND OF THE INVENTION

Various systems have been developed to automatically fill large quantities of prescription bottles for use primarily in mail order pharmacies. Such systems can significantly reduce the time, expense and error rate associated with manual prescription dispensing.

For example, U.S. Pat. No. 5,208,762 to Charhut describes an automated prescription bottle filling system (sold by Automed Technologies, Inc., under the trademark OPTI-FILL®). The system automatically fills, labels, caps, and sorts prescription bottles in accordance with prescription orders stored in a database. Some automated prescription dispensing systems are pallet-based. Pallets loaded with empty prescription bottles are transported to dispensers containing various prescription drugs where each bottle is filled with the prescription corresponding to the prescription information on the bottle label. An example of a pallet or carrier based system is the AUTOSCRIPT II™ system originally manufactured by Automated Prescription Systems (now McKesson Automated Prescription Systems) in the early 1990s.

Such automated prescription dispensing systems require some manner of quality control to ensure that the system is functioning properly. This quality assurance function is often performed by a pharmacist. Computerized systems have been developed to aid pharmacists in checking the accuracy of the prescriptions. For example, Williams, et al., U.S. Pat. No. 5,597,995, discloses a prescription checking work station, which includes a bar code scanner. To check the prescription, the pharmacist first scans a bar code on the bottle label, which retrieves data regarding the prescription. The retrieved data includes a digitized image of the original script and a reference image showing what the prescribed drug should look like. The retrieved information and reference image are displayed on a computer screen. The pharmacist checks the prescription before it is given to the customer by visually inspecting the contents of the bottle to ensure that it is consistent with the original script and reference image.

Prior systems have also been developed to capture a digital image of the contents of the prescription bottle. Mail order pharmacies have employed systems that automatically scan the bar code on the bottle and photograph the contents of the filled bottle before capping. The pill image is linked to the a bar code on the bottle and stored in a database record associated with the prescription order. During the quality control process, the checking pharmacist can scan the bar code on the bottle to retrieve the image of the contents alongside a reference image. The image of the contents can then be compared to the reference image during the quality control process, without opening the bottle.

Such checking systems have a number of significant shortcomings. For example, in order to read the label information and scan the bar code on the bottle, the checking pharmacist must physically handle the bottle. This physical handling introduces an opportunity for human error. A major benefit of automated prescription dispensing systems such as that described in Charhut is the accuracy of such systems. Generally, the introduction of human intervention at any step along the fulfillment process increases the error rate. Thus, the increase in human error rates associated with the physical handling can defeat the purpose of the quality control system. Human handling also increases the opportunity for theft or other breaches of security, which is of particular concern when filling prescriptions for controlled substances. Furthermore, the pharmacist must be present at the place where the bottles are being filled to physically scan and inspect the bottle. For the foregoing reasons, there is a need for a system that allows the pharmacist to check the accuracy of prescriptions being dispensed from a remote location without physically handling the bottles.

The system described herein allows the pharmacist to conduct a quality check without handling prescription bottles or even removing them from the automated dispensing system. It enables the pharmacist to verify the accuracy of a prescription from any location with a computer. It also improves record keeping and allows a pharmacists or customer service representatives to view the complete bottle while talking to a customer on the telephone. These are among the advantages provided by the invention.

SUMMARY OF THE INVENTION

The present invention provides an imaging system for use in a prescription fulfillment process. The system includes a pill camera for capturing an image of pills dispensed into a prescription bottle and a label camera for capturing an image of the bottle label. The pill and label images are stored in a record on a storage device in communication with the cameras. The images can be used to verify that the pills in the bottle correspond with the prescription.

The system preferably includes a computer. The computer retrieves the label image and reads a machine readable code (e.g., a bar code) captured on the label image. The images are associated with the prescription using the code. Alternatively, the system can include a bar code reader for reading the bar code on the label.

The computer can also be programmed to retrieve the label image and pill image and to display the images on a screen. Label data used to print the label and/or a reference image associated with the prescribed drug can also be displayed.

The system can also include a bottle lift and rotate mechanism for lifting and rotating the bottle in front of the label camera so that the label camera can capture the image of the label as the bottle rotates. In one embodiment, the lift and rotate mechanism comprises a vertically movable upper bearing plate having a circular cavity therein for receiving a neck portion of the bottle. The upper bearing plate can be lowered onto the top of the bottle and the bottle neck received into the cavity. A lower lift pusher positioned below the bottle, is raised to engage the bottom of the bottle and lift the bottle in front of the label camera such that the bottle is sandwiched between the upper plate and the lower lift pusher. The lower lift pusher can also include a rotate mechanism for rotating the pusher after it engages and lifts the bottle such that the bottle is rotated in front of the label camera to facilitate capture of the label image. Various alternative lift and rotate mechanisms can be used.

The lower lift pusher preferably includes an encoder for monitoring the rotation of the bottle. A line scan camera can be used to capture the label image. The line scan camera takes a plurality of images of portions of the label as it rotates based upon rotational information communicated by the encoder. The label image is composed from the plurality of images.

In one embodiment, the imaging system is used with a prescription fulfillment process performed by an automated prescription dispensing system comprising pallets holding prescription bottles in rows and columns. This embodiment of the system can simultaneously capture and store images from an entire row of bottles. The system includes a plurality of pill cameras arranged in a row for capturing an image of the pills in a row of bottles before capping. A plurality of label image cameras are arranged in a row for capturing an image of the labels. The system includes a lift and rotate mechanism having an upper bearing plate and a plurality of lower lift pushers. The upper bearing plate has a plurality of circular cavities arranged in a row to receive a row of bottles. The plurality of lower lift pushers are arranged in a row such that they can lift a row of bottles out of the pallet and position them to allow the label image cameras to capture images of the labels of the row of bottles. The images are stored on a storage device in a database record for the associated prescription. An indexing mechanism indexes the pallet forward row by row such that the system can sequentially capture the label images of each row of bottles on the pallet.

The invention further provides a method for monitoring a prescription fulfillment process. An image is captured of pills dispensed into a prescription bottle. An image of the label is also captured. The two images are stored in a record associated with the prescription. The images can be retrieved and displayed on a screen along with label data, drug data, and/or a reference image.

The method can also include the step of reading a machine readable code (e.g., a bar code) on the bottle. The captured images are associated with the prescription using the machine readable code.

The method can also include the steps of lifting and rotating the bottle to facilitate capture of the image of the bottle label. The speed of rotation of the bottle is preferably monitored. A plurality of images of portions of the label are captured as the bottle rotates and the label image is composed of the plurality of images.

The method can be performed by an automated dispensing system comprising pallets holding prescription bottles in rows and columns. In this embodiment, the step of lifting and rotating the bottle can comprise lifting and rotating a row of bottles such that the label images of the row of bottles can be captured. The pallet is indexed forward row by row so that the label images of all rows of bottles on the pallet can be captured sequentially.

BRIEF DESCRIPTION OF THE DRAWINGS

These and other features, aspects and advantages of the present invention will become more fully apparent from the following detailed description, appended claims, and accompanying drawings where:

Figure 1:
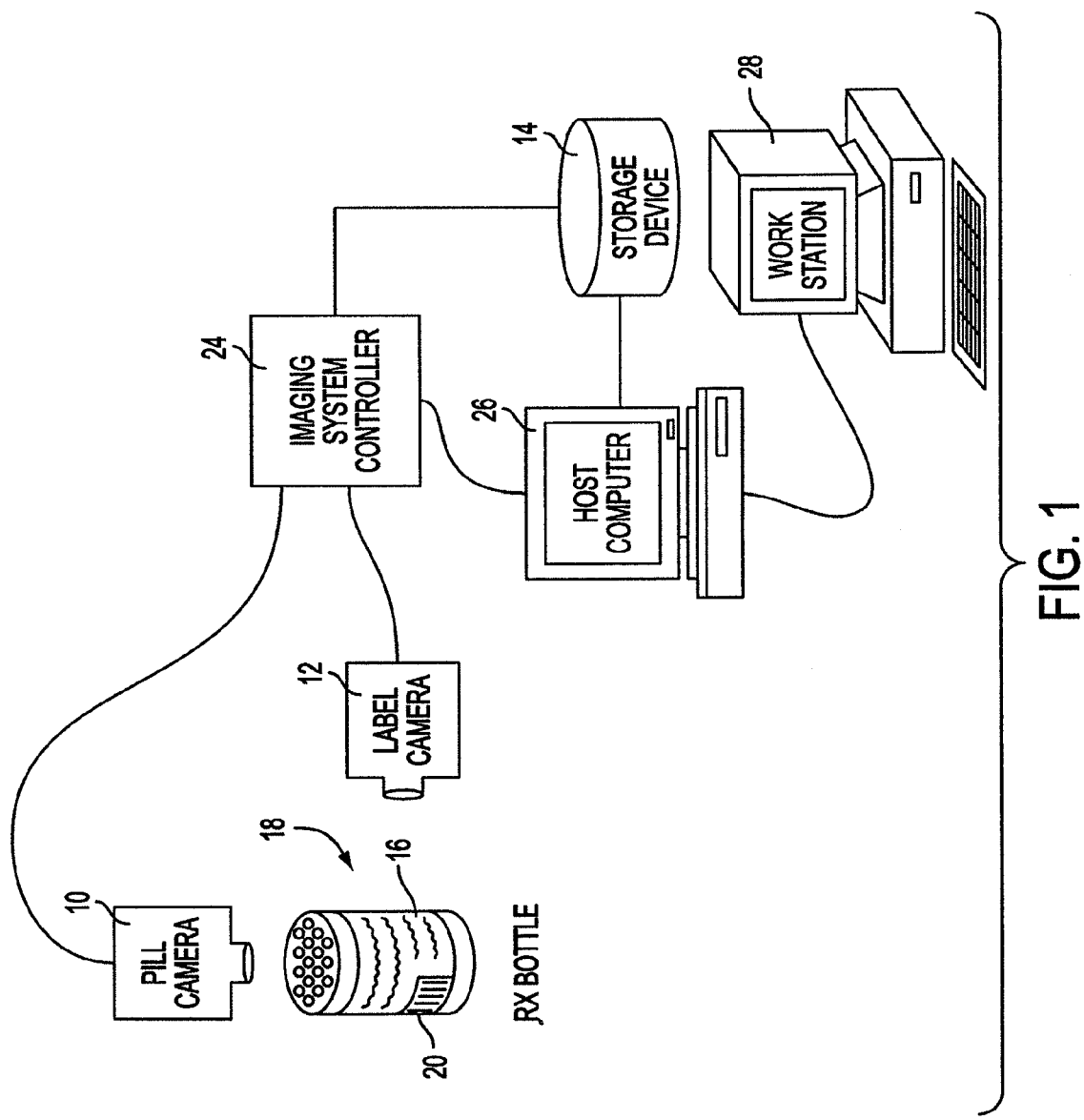
FIG. 1 is schematic illustration of a prescription bottle imaging system.

For clarity, the drawing figures illustrate the general configuration of a preferred embodiment of the system. Descriptions and details of well-known features are omitted to avoid unnecessarily obscuring the invention. The drawings are provided for illustrative purposes only and should not be used to unduly limit the scope of the invention.

DESCRIPTION

The invention is directed to a prescription imaging system and method for capturing, storing and displaying images of prescription bottles during the prescription fulfillment process to monitor the quality of the fulfillment process. The system and method are preferably incorporated into an automated prescription dispensing system. However, the system and method can also be used with manual prescription dispensing processes.

As shown schematically in FIG. 1, an imaging system generally comprises a pill camera 10 a label camera 12 and storage device 14. The pill camera 10 captures a digital image of the contents of a pill bottle 18. The label camera 12 captures a digital image of the bottle label 16. The pill image and the label image are stored in a database record associated with the prescription on storage device 14.

The various components of the imaging system are controlled by a computer controller 24, which is in communication with a host computer 26. Controller 24 and host computer 26 are also in communication with storage device 14 and are programmed to store and retrieve data from storage device 14. A pharmacist or customer service representative can retrieve prescription data, including the stored images, using a work station 28 in communication with the host computer 26. Work station 28 can be located at the same location as the dispensing system or can be remotely located, communicating with the host computer 26 via a network connection such as an intranet or Internet. By retrieving and displaying the pill image and label image, along with other data associated with the prescription, the system allows the pharmacist to conduct a quality check without handling the prescription bottles or even removing them from the dispensing system.

Figure 2:
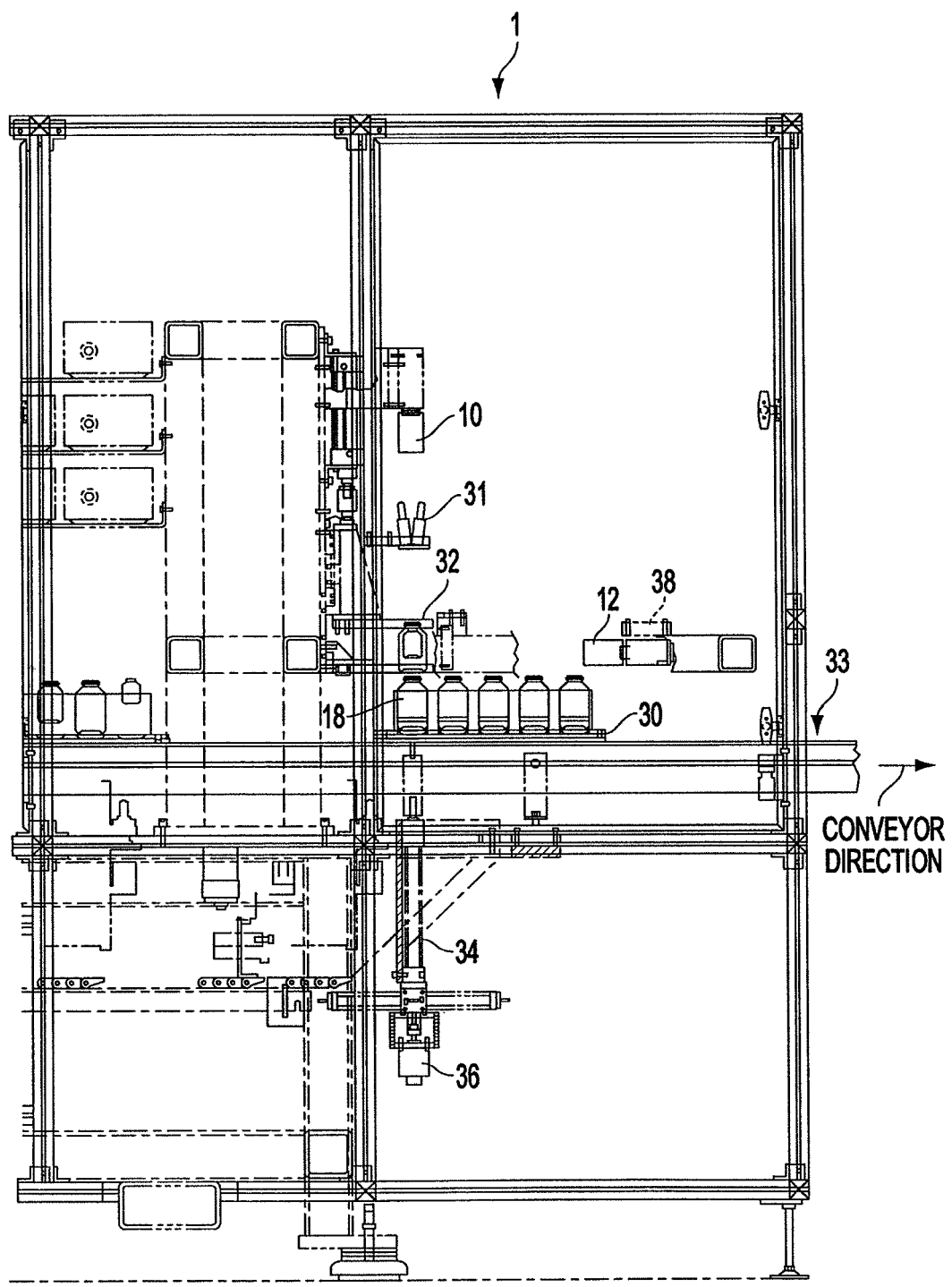
FIG. 2 is a side view of a prescription bottle imaging system.
Figure 3:
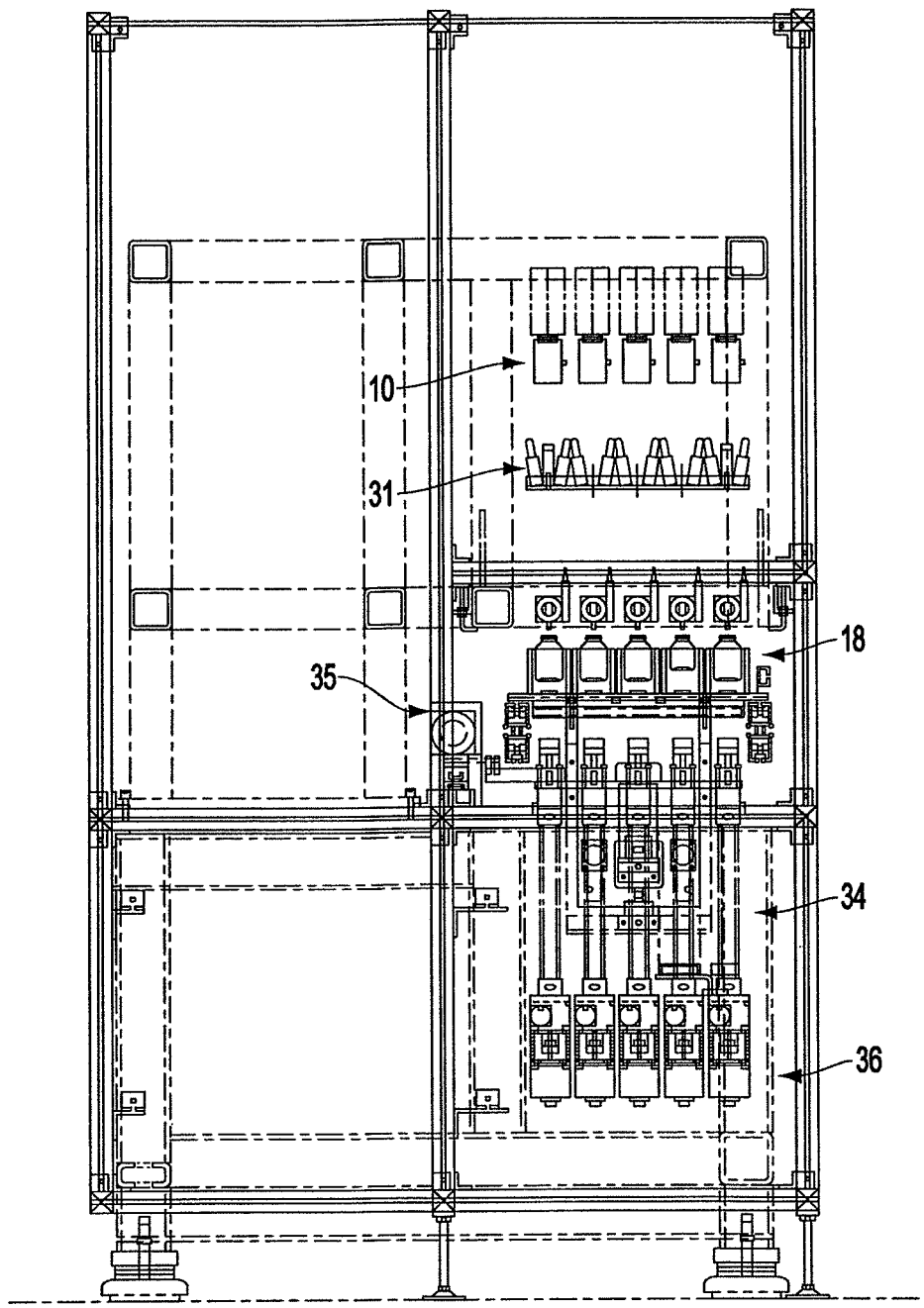
FIG. 3 is a front view of a prescription bottle imaging system.

FIGS. 2 and 3 illustrate an embodiment of the system for use with an automated prescription dispensing system such as the system described in Charhut et al. U.S. Pat. No. 5,208,762, which is incorporated herein by reference in its entirety. The imaging system 1 is preferably positioned on a conveyor lane between the filling station and the capping station so that images of the filled prescription bottles can be captured before the bottles are capped.

The embodiment of the imaging system shown in FIGS. 2 and 3 is configured to operate with a pallet-type dispensing system in which the bottles to be filled are loaded onto a pallet 30 in rows and columns. The system can alternatively be configured to accommodate a single bottle conveyor type system, which does not utilize pallets. In the illustrated embodiment, pallet 30 is configured to accommodate 25 bottles in 5 rows, with 5 bottles in each row. The imaging system 1 can capture images from an entire row of bottles 19 at a time.

Pallet 30 is moved into station by conveyor 33 where the pallet is temporarily stopped by a pneumatic lift mechanism.

A programmable drive indexing mechanism 35 moves the pallet forward row by row through the imaging system.

The system 1 includes five pill cameras 10 in a row positioned above the pallet 30. Each pill camera 10 is positioned above a bottle 18 in a row on pallet 30 so as to capture images of pills dispensed into one of the bottles in the row. The term "pill" is used herein generally to refer to any drug (e.g., pills, capsules, tablets, lozenges, etc.) and the term "bottle" is used to refer generally to any drug container (e.g., bottles, vials, boxes, etc.). The pill cameras can capture a digital image of the contents of each bottle and transmit the image to storage device 14 (see FIG. 1). Upper lights 31 illuminate the inside of the bottle.

Five label cameras 12 are positioned in a row so as to capture an image of the label of each bottle in the row 19. The label cameras 12 are positioned slightly above the plane of the pallet 30 so as to capture the images of the labels after the row of bottles has been lifted out of the pallet 30. The label cameras 12 are preferably line scan cameras capable of capturing images on cylindrical or other curved containers.

A bottle lift and rotate mechanism lifts and rotates the row of bottles 19 to facilitate capture of the label images. In the illustrated embodiment, the lift and rotate mechanism includes an upper bearing plate 32 having a row of five circular cavities therein for receiving a neck portion of each bottle. The upper bearing plate 32 is lowered onto the top of the row of bottles and the bottle necks are received into the cavities. Five lower lift pushers 34 are arranged in a row below the row of bottles. The lift pushers are raised to engage and lift each bottle such that the bottles are sandwiched between the upper plate 32 and the lower lift pushers 34. The bottles are positioned such that all closure ends (threaded finish) are at a similar height for all bottle sizes. The bearing plate 32 is raised and the pushers 34 follow the plate 32. Bottles are held firmly between the plate 32 and the pushers 34. When the plate 32 reaches the top position, the pill cameras 10 take a picture of the bottle contents (pill image). The bottle contents are lighted by upper lights 31.

Each bottle 18 is preferably rotated to facilitate capture of the label image on the curved surface of the bottle. In the illustrated embodiment, each lift pusher 34 includes a rotate mechanisms for rotating the pusher, which in turn rotates the bottle. Various other mechanisms can also be used to rotate the bottle (e.g., an external friction drive). Encoders 36 in communication with each of the plurality of label cameras monitor the rotation of each bottle and communicate information relating to the rotational speed to the label cameras so that the label cameras take a series of images (approximately 1000) of portions of each label as it rotates based upon rotational information communicated by the encoder. The label image is then composed of the plurality of images taken by the line scan camera. Since the rotational velocity and acceleration profile of the bottle surface is variable, each encoder precisely defines a set rotational distance for the camera. This insures a quality image based on consistent spacing. The label scan image is lighted by a set of lower lights 38. After the images have been captured, the upper plate 32 and lower pushers 34 are lowed together to place the bottles back in the pallet. Indexing mechanism 35 moves the pallet 30 forward row by row so that the system can sequentially capture the pill and label images of all rows of bottles on the pallet.

The images are preferably linked to the prescription record associated with the bottle using software stored on controller 24 that reads the bar code from the digitized label image. Alternatively, the system can include a plurality of bar code readers for reading the bar codes on the labels of the row of bottles.

Figure 4:
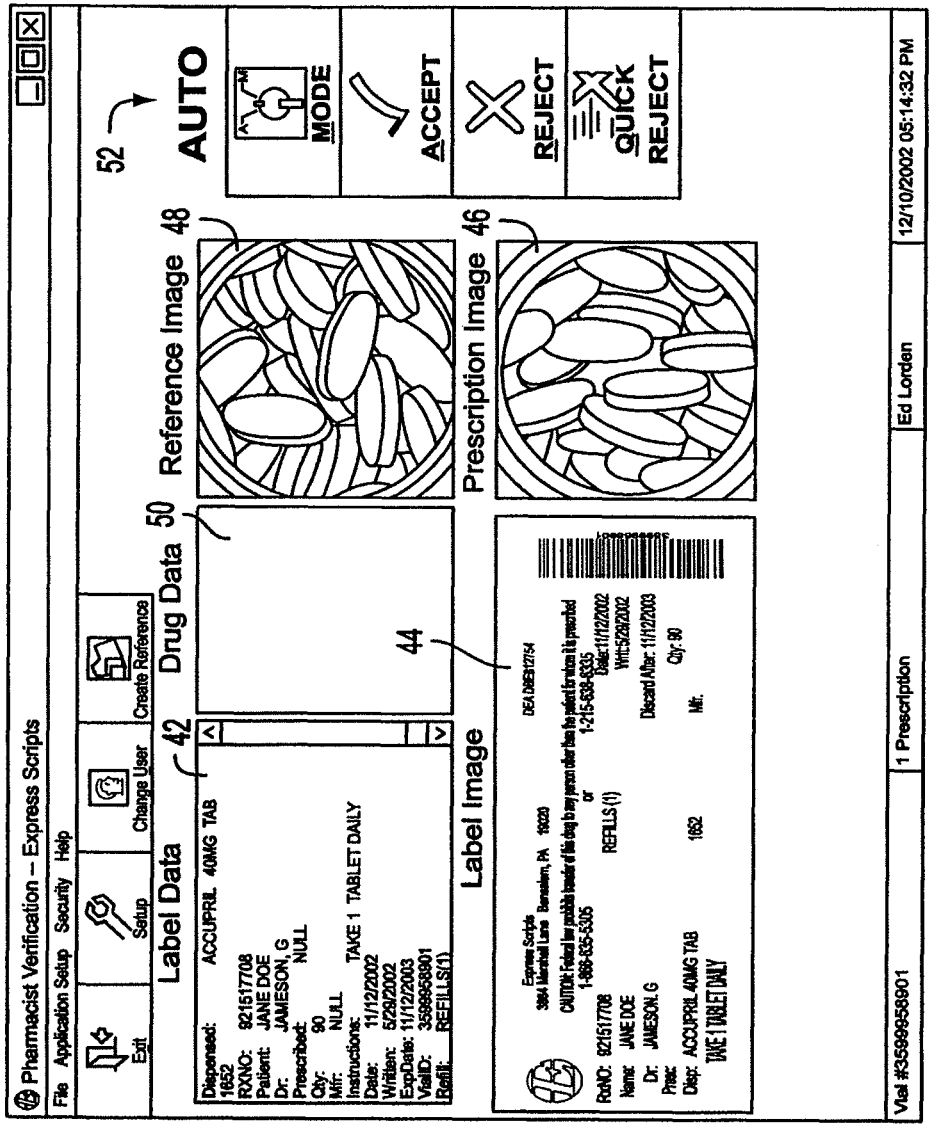
FIG. 4 is an example of a user interface of a quality control program.

Pharmacists and/or customer service personnel can retrieve and view the images and other data relating to the prescription via a local or remote work station 28 in communication with the host computer 26. FIG. 4 shows an example of a screen of a user interface for a quality control application. The screen includes label data 42 retrieved from the prescription record. The label data 42 is the data input into the automated prescription dispensing system for filling the prescription. The system also displays the label image 44 and pill image 46 captured by the cameras of the imaging system. The prescription database can also contain a reference image 48 for the prescribed drug, which is displayed so that the pharmacist can ensure that it matches the pill image 46. The system can also be programmed to retrieve and display drug data 50 relating to the prescribed drug for reference by the pharmacist or customer services personnel. The user interface can also include function buttons 52 for use during the fulfillment process to allow a reviewing pharmacist to accept or reject the prescription. The prescription data is preferably stored in a database so that it can be accessed both during the fulfillment process and afterwards (e.g., by customer service personnel to respond to customer inquiries).

Although the invention has been described with reference to a specific embodiment, it will be understood by those skilled in the art that various changes may be made without departing from the spirit or scope of the invention. For instance, the numerous details set forth herein relating to the embodiment for use in connection with a particular palletized automatic prescription dispensing system are provided to facilitate an understanding of the invention and are not provided to limit the scope of the invention. Accordingly, the disclosure of the embodiment of the invention is intended to be illustrative of the scope of the invention and is not intended to be limiting. It is intended that the scope of the invention will be limited only to the extent required by the appended claims.

What is claimed is:

1. A system comprising:
    a first capture device having a first orientation and positioned above a path to capture first image data of a prescription container at a particular position, the first image data including a prescription drug contained within the prescription container;
    a second capture device having a second orientation and positioned adjacent to the path to capture, at least substantially simultaneously with the first image data, second image data of the prescription container at the particular position, the second image data including a prescription drug identifier; and
    a lift pusher to lift the prescription container through the path into the particular position,
    wherein the second capture device captures the second image data based on operational information associated with the lower lift pusher.

2. The system of claim 1, wherein the first capture device captures the first image data based on lift pusher data.

3. The system of claim 1, wherein the operational information includes rotational information.

4. The system of claim 1, wherein the first image data includes a two-dimensional image of a curved surface of the prescription container.

5. The system of claim 1, wherein the second image data includes a bar code.

6. The system of claim 1, wherein the lift pusher includes a rotation mechanism to allow the second capture device to capture the second image data of the prescription container.

7. The system of claim 1, wherein the lift pusher includes an encoder to monitor the rotation of the prescription container.

8. The system of claim 1, wherein the particular position is a predetermined position.

9. The system of claim 1, wherein the lift pusher lifts the prescription container from a pallet into the particular position.

10. The system of claim 1, wherein the first capture device is affixed in a position above the path and the second capture device is affixed in a position adjacent to the path.

11. The system of claim 1, wherein the second image data includes a prescription drug label, the prescription drug label including the prescription drug identifier.

12. The system of claim 1, wherein the first capture device is a pill camera and the second capture device is a label camera.

13. The system of claim 1, further comprising:
a computing device to store the first image data and the second image data in a record associated with a prescription, the prescription being for prescription drug identified by the prescription drug identifier.

14. A system comprising:
a first capture device having a first orientation and positioned above a path to capture first image data of a prescription container at a particular position, the first image data including a prescription drug contained within the prescription container;
a second capture device having a second orientation and positioned adjacent to the path to capture, at least substantially simultaneously with the first image data, second image data of the prescription container, the second image data including a prescription drug identifier; and
a lower lift pusher to lift the prescription container through the path into the particular position,
wherein the first capture device captures the first image data based on the rotational information associated with the lower lift pusher.

15. The system of claim 14, further comprising:
a computing device to store the first image data and the second image data in a record associated with a prescription, the prescription being for prescription drug identified by the prescription drug identifier.

16. The system of claim 14, wherein the second image data includes a prescription drug label, the prescription drug label including the prescription drug identifier.

17. The system of claim 14, wherein the first image data of the prescription container includes a top view image of the prescription container at the particular position and the second image data of the prescription container includes a side view image of the prescription container.

* * * * *